United States Patent [19]

Sibbald

[11] Patent Number: 4,657,658

[45] Date of Patent: Apr. 14, 1987

[54] SEMICONDUCTOR DEVICES

[76] Inventor: Alastair Sibbald, 38 St. Lukes Road, Maidenhead, Berkshire SL6 7DP, England

[21] Appl. No.: 795,835

[22] Filed: Nov. 7, 1985

[30] Foreign Application Priority Data

Nov. 7, 1984 [GB] United Kingdom ............... 8428138

[51] Int. Cl.$^4$ .......................................... G01N 27/30
[52] U.S. Cl. .................................... 204/406; 204/408; 204/412; 204/416; 204/418; 307/310; 307/491; 324/71.6; 328/1; 357/25; 435/817
[58] Field of Search ................. 357/25; 307/310, 491; 328/1; 204/406, 408, 412, 416, 418; 324/71.6; 435/817

[56] References Cited

U.S. PATENT DOCUMENTS 3,703,650 11/1972 Kendall ............................ 307/310
4,385,274 5/1983 Shimada et al. ................... 324/71.6

*Primary Examiner*—G. L. Kaplan
*Attorney, Agent, or Firm*—Cushman, Darby & Cushman

[57] ABSTRACT

A semiconductor integrated circuit for sensing a physico-chemical property of an ambient includes a pair of semiconductor devices (Q1, Q2) having a similar geometric and physical structure, one device (Q1) being sensitive to the property, the other being insensitive to the property, together with a differential amplifier (A1, A2, A3, A4, A5) having feedback connection to one of the pair of semiconductor devices.

8 Claims, 5 Drawing Figures

$[Ca^{2+}] = 10^{-3} M$
23°C; 10kΩ load
$V_S = \pm 5V$

SEMICONDUCTOR DEVICES

FIELD OF THE INVENTION

This invention relates to semiconductor devices and, in particular, to semiconductor devices capable of the detection and measurement of physico-chemical properties. "Chemical properties" as used herein shall be understood to include ion activity and concentration, presence and concentration of enzymes, substrates, antibodies, antigens, hormones and reproducible gases and the pressure, concentration and activity of chemical and biochemical systems including the constituents of enzymatic systems such as serum enzymes, glucose, lactates, pyrurates, creatinine, urea and the constituents of the immunilogical system.

BACKGROUND OF THE INVENTION

The direct integration of semiconductor devices with a variety of electroactive materials has made possible a new generation of microelectronic sensor devices. The most frequently used vehicle for this work has been the field-effect transistor (FET) in its various forms. Of these, the one most frequently adopted has been the insulated-gate FET. Typical devices are those disclosed in UK Pat. No. 1529743 and U.S. Pat. Nos. 4,411,741 and 4,437,969.

Hitherto, difficulty has been experienced with electrochemical sensing semiconductor devices due (a) to the inherent thermal sensitivity of FET structures, (b) non-linear response due to superposition of a chemically-derived signal on the intrinsic device transfer characteristics and (c) the unsuitability of existing devices for driving multiplexing circuitry where fast voltage transients may be present.

These problems have now been overcome with a novel integrated device structure.

SUMMARY OF THE INVENTION

According to the present invention, there is provided a semiconductor integrated circuit including a first semiconductor device sensitive to a physico-chemical property of an ambient to which it is exposed and capable of producing an output signal dependent on said physico-chemical property, a second semiconductor device insensitive to said physico-chemical property but having a geometry and physical structure substantially identical with that of said first semiconductor device and being coupled thermally to said first semiconductor device together with differential amplifier means the input of which is coupled to the outputs of said first and second semiconductor devices and the output of which is coupled to the input of one of said first and second semiconductors.

BRIEF DESCRIPTION OF THE DRAWINGS

The invention will now be particularly described by way of example with reference to the accompanying drawings in which.

DETAILED DESCRIPTION OF THE INVENTION

Figure 1:
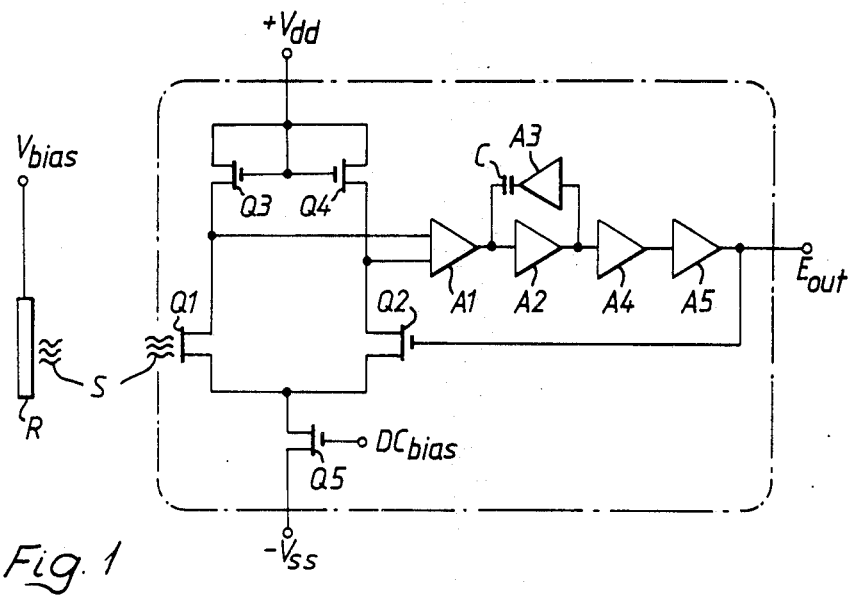
FIG. 1 is a schematic diagram of an integrated circuit.

A practical embodiment of a device in accordance with the invention in the form of an operational transducer is illustrated in FIG. 1. A chemical-sensing field-effect transistor Q1 configured to be non-inverting and exposed to solution S and an insulated-gate field-effect transistor Q2 configured to be inverting were connected to a differential amplifier A1 feeding a cascade amplifier A2 with a source follower loop A3,C. The high output impedance of the cascade amplifier was matched by a source follower stage A4 to the low input impedance of an output amplifier A5. Feedback from the output stage to the control electrode of the insulated-gate FET Q2 provided compensation for thermal effects, which are rejected as a common-made signal.

The electrochemical potential of the ambient solution phase to which the transducer is exposed is maintained at a constant value with respect to that of the semiconductor substrate of the operational transducer by means of a reference electrode R connected to a bias voltage source $V_{bias}$.

Electron-beam lithography was used to write the designs onto the mask set used for processing. Devices were fabricated on 75 mm diameter, p-type, 14–20 ohm cm, (100) orientation silicon wafers, using a modified n-channel MNOS process. The gate dielectric comprised 500 Å thermally grown $SiO_2$, overlain by 900 Å silicon nitride (deposited by low pressure constant voltage . . . at 800° C.). Half of the wafer batch were given light, n-type channel ion-implants (depletion mode), and the remainder were lightly implanted with p-type impurities (enhancement-mode); resultant threshold voltages ($V_T$) were approximately $-1.0$ V and $+1.0$ V respectively. A p-type channel-stopper implant was incorporated, and a 6,000 Å thick film of polyimide was used for a final, protective overlay, with only the bonding pads and ChemFET gate area remaining exposed. The die size was $2.03 \times 2.43$ mm.

The operation transducer chip includes a $72 \times 484$ μm aperture in the polyimide overlay for the ChemFET gate; the channel dimensions were $12 \times 432$ μm, and the gate area was surrounded by three concentric octagonal frames (600, 700 and 800 μm diameter), for targetting ink dots which was used during polyimide/-photopolymer encapsulation.

The operational transducers were mounted and wire bonded onto the tips of 9 mm $\times$ 94 mm printed-circuit board substrates, so as to form dip-type sensors for electrochemical evaluation, and were selectively encapsulated using either H-54 epoxy resin, or a polyimide/-photoresist composite, leaving only the $Si_3N_4$ surface of the active gate region exposed.

The silicon nitride gate dielectric surface of the transducer is intrinsically pH-responsive (3,44). Potassium-responsive transducers were made by casting, from solution, an ionophore-doped, polymeric film (by weight: 1% valinomycin; 66% bis(2-ethylhexyl)adipate; 33% poly(vinylchloride)), over the exposed gate, using cyclohexanone as the solvent. A single drop of the doped-polymer solution was applied to each gate, and then the solvent was removed by vacuum desiccation for 12 hours at ambient temperature. The resultant films were approximately 50 μm thick.

Figure 2:
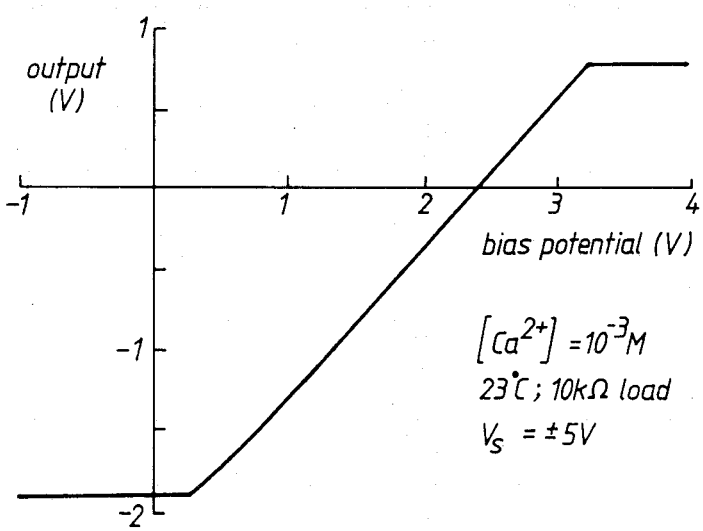
FIGS. 2 to 5 show measurements obtained with different devices and electrolytes.

The transfer characteristics of a typical transducer made by the above process (in this instance, a $Ca^{2+}$-responsive transducer, incorporating a calcium ionophore-(ETH 1001) doped, polymeric gate) are shown in FIG. 2. The transducer has unity gain between the saturation and pinch-off limits of the internal output driver stage, which is generally in the range $-3$ V$<$-

$E_{out} < +1$ V for $V_S = \pm 5$ V. When an aluminium gate is used instead of a chemical-sensing electroactive material, in order to permit characterizations by direct electrical control, the input offset voltage lies typically in the range $-30-+120$ mV, however a relatively large input offset voltage is invariably observed in the chemoresponsive transducer characteristics, and is usually in the range $+1-+2.5$ V. This is due to the difference in threshold voltages between the metallized-gate/$Si_3N_4$-gate differential pair, which is caused by the electrochemical differences in gate contact mechanism, and is largely unimportant (viz. the matching is not affected). There is only a very slight optical sensitivity; a change from ambient illumination to darkness results in a $-3$ mV change in output signal.

Figure 3:
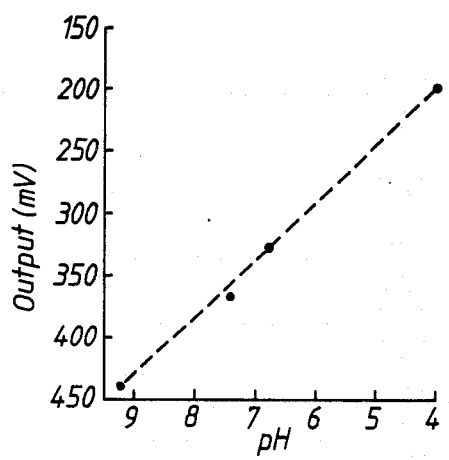

The electrochemical response of a pH-sensitive transducer (i.e. having a $Si_3N_4$ gate), is shown in FIG. 3, over the range pH 4 to pH 9.2. The response is linear, but somewhat sub-Nernstian (46.2 mV/decade), however the latter is a common feature of field-effect sensors having $Si_3N_4$ as the electroactive gate material. Devices with $Si_3N_4$ gates have been found to operate satisfactorily throughout the range pH 1 to pH 14. The rate of response to a step change in pH was too rapid to sensibly quantify; being several hundreds ms, at most.

Figure 4:
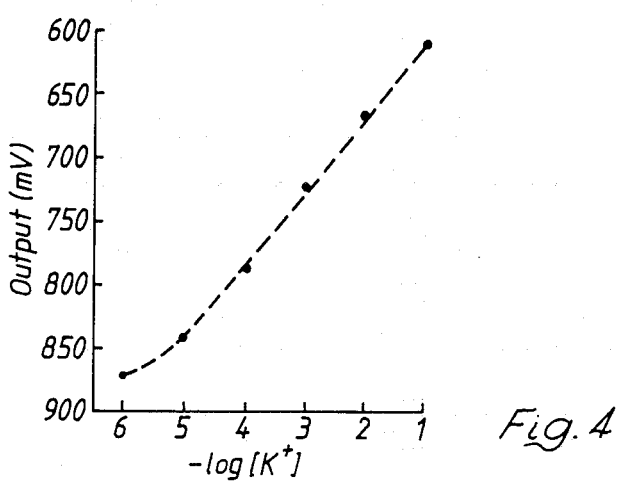
Figure 5:
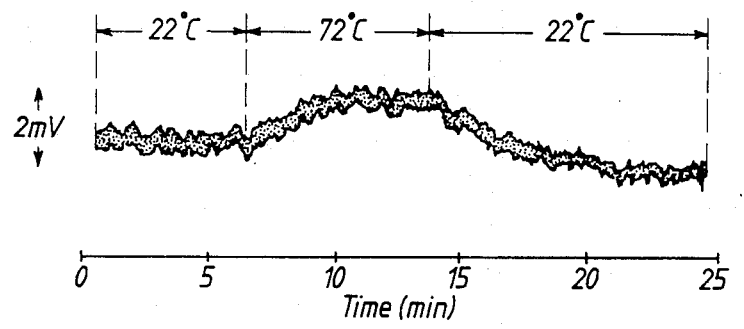

The electrochemical characteristics of a $K^+$ transducer are shown in FIG. 4. The response is virtually Nerstian over the $K^+$ concentration range $10^{-1}-10^{-5}$ mol $l^{-1}$, having a slope of 57.8 mV/decade; the response time is, again, too rapid to quantify (<500 ms). The $H^+$ and $K^+$ transducers are not subject to any hysteresis or spurious, small voltage offsets caused by dipping between solutions of disconnecting the reference electrode, as discrete ChemFET devices are prone to be when operated in constant current mode. A stable output potential was established almost instantaneously when the transducer is placed in solution.

The thermal characteristics of a transducer having an aluminium gate biased to 0V are shown in FIG. 3. The output signal was recorded at ambient temperature (22° C.) for 6 minutes, then the transducer was placed in an oven, thermostatted at 72° C.; 4 minutes later, the output potential was again stable after a 1.2 mV shift (viz. the input offset voltage thermal coefficient is approximately 24 $\mu V°C.^{-1}$), then 3 minutes later the transducer was returned to ambient temperature. A very small background signal drift (<1.5 mV hr$^{-1}$) was apparent, and can be attributed to burn-in effects. This drift was exacerbated by the application of epoxy or thick polyimide films onto the chip surface, (in this case, directly onto the metallization), and was probably caused by the formation of surface leakage currents, owing to the presence of impurities or moisture, hence incorporation of a wafer-level, protective $SiO_2$ overlay film would give improved results. The low frequency noise present in the output signal was approximately $\pm 0.1$ mV in magnitude.

Alternative and additional methods may be used in the fabrication of the transducers. For example, their film techniques such as vacuum evaporation and sputtering, chemical vapour deposition, spin-coating, etc., can be used to deposit both inorganic and organic gate materials, including metal oxides and halides, ionophore-doped polymeric films and others, where the resultant film would be too fragile or insufficiently conductive for use in a conventional ion-selective electrode.

The operational transducer concept is not limited to ion-selective sensor applications, and is compatible with any type of discrete field-effect chemical sensor, including enhancement and depletion-mode FETs, offset gate FETs, junction FETs, gapped-gate devices, suspended mesh variants and devices with electrostatic gate protection. Neither are the devices nor is it restricted to implementation using an NMOS process, the use of CMOS technology would permit a simpler design having fewer transistors. Other worthwhile developments would be the inclusion of electrostatic protection and on-chip temperature measurement, and the fabrication of a multi-function operational transducer array for the simultaneous measurement of several different species, such as $H^+$, $K^+$ and $Na^+$.

What is claimed is:

1. A semiconductor integrated circuit including:
   a first semiconductor device sensitive to a physicochemical property of an ambient to which it is exposed and capable of producing an output signal dependent on said physico-chemical property,
   a second semiconductor device insensitive to said physico-chemical property but having a geometry and physical structure substantially identical with that of said first semiconductor device and being substantially in isothermal contact with said first semiconductor device, and
   differential amplifier means having an input coupled to outputs of said first and second semiconductor devices and having an output coupled to an input of one of said first and second semiconductors.

2. A semiconductor integrated circuit as claimed in claim 1 wherein said first and second semiconductor devices are field-effect transistors.

3. A semiconductor integrated circuit as claimed in claim 2 wherein said first semiconductor device includes a silicon substrate having channel region overlain by a layer of silcon nitride.

4. A semiconductor integrated circuit as claimed in claim 3 wherein said first semiconductor device includes a layer of silicon dioxide between said layer of silicon nitride and said substrate.

5. A semiconductor integrated circuit as claimed in claim 4 further including a layer of an ion-sensing polymeric film overlaying said layer of silicon nitride.

6. A semiconductor integrated circuit as claimed in claim 5 wherein said polymeric film incoporates an ionsphere dopant.

7. A semiconductor integrated circuit as claimed in claim 6 wherein said ionsphere-doped polymeric film includes valinomycin, bis(2-ethylexyl)adipate and polyvinyl chloride.

8. A semiconductor integrated circuit as claimed in any one of claims 1-7 having a protective overlay of polyimide.

* * * * *